United States Patent [19]

Neirinckx et al.

[11] Patent Number: 4,830,848

[45] Date of Patent: May 16, 1989

[54] RADIOPHARMACEUTICAL COMPOSITION CONTAINING TANTALUM-178 AND PROCESS THEREFOR

[75] Inventors: Rudi D. Neirinckx, Medfield; B. Leonard Holman, Chestnut Hill; Michael A. Davis, Westwood, all of Mass.; Gale I. Harris, East Lansing, Mich.

[73] Assignee: Massachusetts Institute of Technology, Cambridge, Mass.

[21] Appl. No.: 27,573

[22] Filed: Mar. 19, 1987

Related U.S. Application Data

[63] Continuation of Ser. No. 314,614, Oct. 26, 1981, abandoned, which is a continuation of Ser. No. 147,809, May 5, 1980, abandoned, which is a continuation of Ser. No. 943,883, Sep. 19, 1978.

[51] Int. Cl.$^4$ .................. A61K 49/02; B65D 69/00; C09K 11/04
[52] U.S. Cl. .................. 424/1.1; 206/569; 252/645
[58] Field of Search .............. 424/1.1, 9; 206/569; 252/645

[56] References Cited

PUBLICATIONS

Holman et al, Chemical Abstracts, vol. 89 (Jul. 10, 1978), No. 13472t.

*Primary Examiner*—John S. Maples
*Attorney, Agent, or Firm*—Paul J. Cook

[57] ABSTRACT

A physiologically acceptable solution of tantalum-178 having an activity of 0.1 to 200 millicuries per milliliter of tantalum-178 solution is provided. The solution is obtained from tungsten-178 bound to a column of an anion exchange resin which forms tantalum-178 in situ by eluting the column with a hydrochloric acid solution containing hydrogen peroxide to form an acidic solution of tantalum-178. The acidic solution of tantalum-178 then is neutralized.

8 Claims, No Drawings

RADIOPHARMACEUTICAL COMPOSITION CONTAINING TANTALUM-178 AND PROCESS THEREFOR

The Government has rights in this invention pursuant to Contract Number E(11-1)-4115 awarded by the Department of Energy.

This is a continuation of co-pending application Ser. No. 314,614, filed on Oct. 26, 1981, now abandoned, which is a continuation of Ser. No. 147,809, filed May 5, 1980, now abandoned, which is a continuation of Ser. No. 943,883, filed Sept. 19, 1978.

BACKGROUND OF THE INVENTION

This invention relates to radiopharmaceutical compositions containing tantalum-178 and to a method and kit for preparing such compositions.

Radiochemistry presently is utilized in biological research and medical diagnosis. Certain radioactive preparations, when introduced into a biological system, will localize in specific organs, tissues or skeletal material. With radiation detecting devices such as a gamma camera or a high pressure, multiwire proportional camera, the target areas are visualized and the functioning of certain organs such as the heart, the kidney or the liver then can be monitored to diagnose a particular disease or structural defect in the biological system.

Presently, the preferred isotope for use in radiopharmaceutical preparations is technetium-99m (Tc-99m). Technetium-99 has a high specific activity which makes it possible to visualize deep organs, yet the radiation is easily collimated. It has a half-life of 6 hours which makes it useful for many diagnostic purposes. However, its use is not desirable in certain patients such as pediatric patients since even with this half-life which is considered relatively short, the radiation to which the pediatric patient is exposed may be unsafe.

Accordingly, it would be highly desirable to provide radiopharmaceutical compositions which, when introduced into a biological system can be detected by presently available apparatus and which do not subject the biological system to radiation for extended periods of time. Specifically, it would be desirable to provide such radiopharmaceutical compositions which subject the biological system to radiation to a dosage and for a period of time substantially less than that of technetium-99m.

SUMMARY OF THE INVENTION

This invention provides a physiologically acceptable composition containing tantalum-178 which is useful in the diagnosis of a disease or a structural defect of a biological system, particularly in humans. In addition, the present invention provides a process for preparing these compositions by forming and isolating the parent radioisotope, tungsten-178 and subsequentially separating the physiologically acceptable composition from the tungsten-178. Furthermore, the present invention provides a generator useful for forming physiologically acceptable solutions of tantalum-178 continuously for a limited period of time.

DESCRIPTION OF SPECIFIC EMBODIMENTS

As a first step in the process of this invention, tantalum-181 is exposed to incident proton energy in the manner described in Phys. Rev. C6: 1009–1015, 1972, Siddiqui et al which comprises $^{191}Ta(p,4n)^{178}W$. The energy level of the incident protons is controlled so as to maximize the production of tungsten-178 while minimizing the production of tungsten-177. This is because tungsten-177 decays to tantalum-177 having a half-life of 57 hours, which in turn gives rise to hafnium-177 having a 113-keV gamma ray which is dangerous to many patients exposed to such radiation. Accordingly, the physiologically acceptable tantalum-178 composition utilized in the present invention should comprise less than about 0.05, preferably less than about 0.01 percent of the radioactivity from tantalum-177, based upon the total radioactivity from tantalum-178 and tantalum-177. In order to obtain such compositions, it has been found that the incident proton energy to which the tantalum-181 is exposed should be between about 25 MeV and 100 MeV, preferably between about 32 and 40 MeV, and most preferably 34 MeV. Tantalum-177 and hafnium-177 formed directly or through the decay of tungsten-177 are later separated from tungsten-178 after more than about 99.5%, preferably more than 99.9% of the tungsten-177 has decayed to its tantalum and hafnium daughters. The tantalum-181 exposed to incident proton energy then is dissolved in an acid solution comprising hydrofluoric acid and an oxidant such as nitric acid and/or hydrogen peroxide. This solution is evaporated and the residue is dissolved in an acid solution containing 3N to 9N hydrofluoric acid, preferably about 6N hydrofluoric acid and 0.5 to 10N hydrochloric acid, preferably about 6N hydrochloric acid. The acidic solution then is passed through an anion exchange column which has been equilibrated with essentially the same acidic solution utilized to dissolve the tungsten-178. The tungsten-178 solution then is passed through the column and the eluant rich in tungsten-178 is recovered. High yields of the tungsten-178 can be obtained which are sufficiently pure for subsequent use in forming tantalum-178 solutions which can be administered to biological systems. Suitable exchange materials useful in columns for purifying tungsten-178 are strongly basic anion exchange resins.

The purified tungsten-178 solution is evaporated to dryness and then is fixed to an anion exchange column by first forming a solution comprising hydrogen chloride at a normality of between about 0.05 and 0.25, preferably between about 0.1 and 0.15 normality together with an oxidant such as hydrogen peroxide at a concentration of between about 0.05 and 3%, preferably between about 0.05 and 0.15%. This solution is percolated through a pre-equilibrated anion exchange resin in order to load the tungsten-178 onto the resin by anion exchange. The presence of this strong oxidant maintains the tungsten-178 bound to the exchange resin. When it is desired to elute the tantalum-178, the same acid-oxidant solution is used to elute the tantalum-178 from the resin and to separate it from the bound tungsten-178. The anion exchange resin utilized for this purpose is in a highly positive form which is formed from a highly positively charged resin such as that charged with quaternary ammonium salt groups, pyridinium salts or the like which is then ionized in an aqueous solution. The tungstate then replaces the hydroxyl groups of the resin. Since mesh size controls the speed of the equilibrium, it is preferred to utilize small size anion exchange resins having a mesh size of between about 200 and 400. The eluted tantalum-178 solution then is neutralized with a basic material such as phosphate, sodium hydroxide, sodium citrate or the like to form a physiologically acceptable composition. The resultant solution of tantalum-178 is physiologically acceptable, contains tantalum-178 having an activity of between about 0.1 and 200 millicuries per milliliter of tantalum-178 solution, preferably between about 100 and 100 millicuries, so that it can be administered to animals including humans such as by intraveneous administration.

The composition for generator elution is a compromise resulting from the required yield of tantalum and the number of elutions that may be made before W-178 breakthrough becomes unacceptable. The oxidant, e.g. hydrogen peroxide is used to reduce W-178 breakthrough—presumably by maintaining the tungsten on the column in the form of tungstate. Although the concentrations of hydrogen peroxide, the preferred oxidant, do not produce observable physiologic effects, the hydrogen peroxide can be destroyed before administration by treating the eluant with sodium bisulfite or the like or by heating.

Some tungsten breakthrough may occur immediately after loading the column and also after leaving the column standing for several hours. However, with an eluting solution of 0.1N HCl-0.1% $H_2O_2$, for example, no breakthrough higher than 0.1% is seen in the first eluted fraction after the column had been standing up to 1 week. When the breakthrough from a particular column reaches high levels, the tungsten can be removed by elution with concentrated acid, e.g. about 4 to 12N HCl. This solution can then be evaporated to dryness, the residue redissolved in the acid-oxidant solution, e.g. HCl-$H_2O_2$ and loaded onto a new pre-equilibrated resin bed. After percolating of the latter solution through, the column is ready for use.

In dilute hydrochloric acid soultion, tantalum is normally in colloidal form as a result of the formation of polynuclear complexes; pentavalent tantalum adsorbs strongly on an anion-exchange resin in dilute HCl solution. Under the conditions used herein, the tantalum is soluble or at least is in a form that has little affinity for the resin column; it is therefore possible that the species could be $Ta(OH)_4+$ and/or $Ta(OH)_5$. These are the principal species at pH values lower than 2 in the absence of polynuclear complex formation. The variation in elution yields for tantalum appears to be in reasonable agreement with their reported values for the fraction of $Ta(OH)_4+$ existing in dilute acid solutions. The presence of two species in the eluant, presumably with differing affinities of the column material, could account for the tailing observed on the column. Some contribution would also be expected from the continued production of Ta-178 from its parent W-178 on the column. Batch equilibrium studies with different ratios for resin-to-liquid phase, however, indicate the presence of only one species.

Using Ta-182 as a tracer, the $K_D$ for tantalum was determined to be less than 0.3 for equilibration between the 0.1N HCl-0.1% $H_2O_2$ solution and the anion-exchange resin. On this basis, it appears that all the tantalum should be eluted from the column. The fraction of Ta-178 retained at lower HCl concentrations may represent an unidentified tantalum species that coexists with carrier levels of Ta. The observation that a solution of Ta-182 containing Ta carrier has the same elution profile as the carrier-free Ta-178 supports this hypothesis. Addition of carrier tantalum does not alter the yields or the tailing effect, and neither does prolonged equilibration times in the batch studies. This seems to exclude the possibility of a slow reaction leading to the formation of a strongly adsorbed tantalum species.

The percentage of tantalum collected as a function of eluant acidity is in fair agreement with the fraction of $Ta(OH)_4+$ that would occur in a tantalum solution in the absence of polynuclear complexes. If two species do exist in solution, and if equilibrium were established quickly between them, then upon removal of either one, the yield of the species with low $K_D$, presumably $Ta(OH)_4+$, would reflect its ratio in the equilibrium mixture. The high $K_D$ species remaining on the column would then begin to re-establish the equilibrium so that tantalum would still be eluted giving rise to the observed tailing effect.

The tantalum-178 solutions of the present invention are particularly useful for administration to pediatric patients and for cardiac studies in all patients.

A particularly suitable means for preparing the tantalum-178 solutions of this invention is to provide the elution composition and a physiologically acceptable neutralizing composition in a kit for use in conjunction with a tungsten-178 generator. For example, 0.5 to 3 ml of a solution comprising 0.05 to 0.25N hydrochloric acid and 0.05 to about 3 volume percent hydrogen peroxide, i.e., a lower concentration than that which will form physiologically unacceptable gas bubbles in the blood stream can be hermatically and aseptically sealed in the same having a volume of about 1 to 3 ml. An additional vial which is partially evacuated is provided for the neutralizing agent for the acid such that when the eluting agent containing the tantalum-178 is recovered from the tungsten-178 generator, the neutralizing agent will form a solution which is preferably substantially isotonic with mammalian body fluids, e.g. human blood. The tantalum-178-hydrochloric acid-hydrogen peroxide solution obtained from the tungsten-178 generator is combined with the contents of the evacuated vial containing the neutralizing agent. This is effected conveniently by providing a needle at the bottom of the column which punctures the seal of the evacuated vial to allow the tantalum-178 solution to pass into the vial. The resultant physiologically acceptable solution then can be administered to a patient, for example by injection into the blood stream of the patient.

Conveniently, the vial containing the physiologically acceptable solution is provided with a plunger means and a means for attaching a hypodermic needle so that the vial functions as a hypodermic syringe, whereby, after preparation of the solution, the contents can be injected parenterally without being transferred to another container or syringe.

Radioactive mesurements are made in the conventional manner for a period beginning after injection and lasting from about 15 minutes to about 1 hour.

The following examples illustrate the present invention and are not intended to limit the same.

EXAMPLE I

This example illustrates a process for obtaining tantalum-178.

Five 0.005 in. thick tantalum foils mounted in a pneumatic rabbit assembly were irradiated in a 50 MeV variable-energy sector-focussed cyclotron at an incident proton energy of 40 MeV. With an energy loss of 8 MeV across the target, the energy range of the incident protons thus spanned from 40 to 32 MeV.

Gamma-ray spectra were obtained using a Ge(Li) detector approximately 30 hr after bombardment, when most short-lived activities were negligible.

The irradiated portions of the tantalum foils were cut out and dissolved in concentrated hydrofluoric acid containing nitric acid. This solution was evaporated to dryness, treated with concentrated hydrochloric acid and again evaporated to dryness. The residue was dissolved in 6N HCl-1.5N HF solution and eluted through a pre-equilibrated 200-400 mesh anion-exchange column, Bio-Rad AGl-×8. Spectra of the separated equilibrium samples were obtained using a Ge(Li) low-energy-photon spectrometer (LEPS), a planar crystal of 0.6 cc active volume.

Maximum yields of W-178 activity occurred at $E_p=34$ MeV. The activities et $E_p=39$ MeV and 32 MeV were each 83% of the maximum, indicating less dependence on energy than predicted.

Ge(Li) gamma-ray spectra taken 30 hr after the cyclotron bombardment showed that the relative intensity of the 113-keV gamma ray from Hf-177 decreased rapidly in intensity with decreasing beam energy, varying from 2.4 times that of the 93-keV peak in Hf-178 at $E_p=39$ MeV to 0.16 at $E_p=36$ MeV. At $E_p=35$ MeV and below, the 113-keV peak was practically negligible.

The carrier-free chemical separation of W-178 from the irradiated tantalum targets resulted in yields of about 98%. The dominant features of a Ge(Li)-LEPS spectrum are the intense tantalum and hafnium characteristic radiations following electron-capture decay of W-178 and Ta-178, respectively. Tantalum $K_\beta$ and $K_\alpha$ lines are seen at 56–58 and 65–67 keV, and the corresponding hafnium lines are at 54–56 and 63–65 keV. The 93-keV peak in Hf-178 can be seen at about 1/12 the intensity of the characteristic x-ray radiation. The transition is 83% internally converted, leading to an effective incidence of 6.3% per Ta-178 disintegration. Using this figure, a production figure of approximately 1.1 mCi/$\mu$A-hr per MeV of target thickness was achieved.

The short-lived radionuclide Ta-178 has physical decay characteristics suitable for use in diagnostic nuclear medicine. Furthermore, the half-life of the parent W-178 (21.7 d) is long enough so that this nuclide can form the basis of a generator system for its short-lived product.

This study demonstrates that W-178 can be produced readily, using simple target techniques, in both the quantity and purity that would be demanded in diagnostic nuclear medicine. The optimal average proton energy in the target was 34 MeV, at which energy the (p,5n) product W-177 is negligible. This corresponds to a 38 MeV incident proton energy for a practical target thickness of 8 MeV.

The half-value layers and transmission percentage through 1 cm of tissue are shown in Table I for Ta-178 (Hf-178 characteristic x-rays) and for 80- and 140-keV photons. The transmission percentage through muscle is only 3% less for Ta-178 than for 80 keV photons, but 11% less through bone.

An application for Ta-178 is for cardiac imaging. Accurate assessment of ventricular function requires high count rates when first pass techniques are used. High doses of Ta-178 can be administered when the multiwire proportional counter is used as the detector, thereby obtaining a more accurate assessment of regional wall-motion abnormalities and regional cardiac hemodynamics. Thus, multiple studies can be performed at reasonable intervals under physiologically or pharmacologically altered conditions because of the short half-life of the radiotracer. Since the heart is not a deep-seated organ and can be closely approached by an external detector, and since the multiwire proportional camera is efficient for lower photon energies, tissue absorption is sufficiently offset to warrant further investigation of this use.

TABLE I

| | Energy Level (keV) | | | | | |
|---|---|---|---|---|---|---|
| | 54–56 63–65 (Ta-178) | | 80 | | 140 | |
| | HVL* | % T** | HVL | % T | HLV | % T |
| Muscle | 3.12 | 80 | 3.61 | 83 | 4.32 | 85 |
| Bone | 1.21 | 56 | 1.75 | 67 | 2.37 | 75 |

*Half-value layer (cm)
**Transmission percentage through 1 cm of tissue

EXAMPLE II

This example illustrates the preparation of a pharmaceutically acceptable solution of tantalum-178 useful in diagnosis.

The carrier-free separation of tungsten from the irradiated tantalum targets was carried out by anion-exchange chromatography in a mixture of hydrochloric and hydrofluoric acids by the method of Example I. The irradiated portions of the tantalum target foils were cut out and dissolved in concentrated hydrofluoric acid to which concentrated nitric acid was added in drops until a clear solution was obtained. The solution was evaporated to dryness, the residue taken up in concentrated hydrochloric acid and again evaporated to dryness. The resulting material was redissolved in 6N HCl-1.5N HF soltuion (10 ml/100 mg tantalum) and refluxed for 30 min to ensure that less than 0.1% of the tantalum remained in colloidal form.

A 200–400 mesh anion-exchange column, Bio-Rad AGl×8, 1 cm in diameter and with a height of 3 cm/100 mg tantalum (minimum height 10 cm), was equilibrated with 6N HCl-1.5N HF solution and the target solution eluted through the column. Only tungsten-178 was detected in the eluant. By continuing the elution with another six column volumes of fresh 6N HCl-1.5N HF, 98% of the W-178 was collected.

Elution of the 6N HCl-1.5N HF target solution through the anion-exchange resin gave a 98% yield of carrier-free tungsten, with 99.9% of tantalum retained on the column. The remaining 0.1% of the tantalum was eluted before the tungsten, so that this colloidal tantalum could also be separated from the W-178. The refluxing step described in the procedure is important to minimize the level of this colloidal tantalum.

The tungsten solution obtained above was evaporated to dryness and the residue taken up in 0.15N HCl-0.1% $H_2O_2$ solution. This was percolated through a pre-equilibrated 200–400 mesh anion-exchange column in order to load the tungsten parent. During the initial stages of development, a 9 ml resin bed was used.

In order to test for the optimum yields of Ta-178, eluting solutions were used ranging from 0 to 1N in hydrochloric acid and 0 to 0.2% in peroxide. All samples were counted on a NaI (Ti) detector and the half-life and purity of the eluted activity determined in each case. Breakthrough of the tungsten parent was determined under each of the eluting conditions. High-resolution gamma-ray spectra of the eluted samples were obtained using a 0.6 cc water (Ge(Li) detector.

In addition, the distribution constants ($K_D$) of tungsten and tantalum between the anion-exchange resin and the various mixtures of HCl and $H_2O_2$ were investigated by batch equilibration. The $K_D$ was calculated from the expression $$\frac{\% \text{ metal/g resin}}{\% \text{ metal/g/liquid phase}}$$

The radioactive tracers used in these studies were W-178 and Ta-182.

In order to reduce the volume of eluant from the generator to levels more acceptable for i.v. injection, the resin-bed volume was reduced in later experiments to a maximum of 1 ml. Yields of tantalum and tungsten breakthrough were determined in the same way as for the larger columns.

Preliminary biodistribution studies were performed in rats at 15–20 min after i.v. administration of one column volume of Ta-178 eluant (0.1N HCl-0.1% $H_2O_2$) from the 0.6 ml column, typically using 50 μCi of the radionuclide. Further studies were carried out using eluant solutions adjusted to pH 7 with 4.06% $Na_2HPO_4.7H_2O$ and to pH 5.4 with 3.03% citrate buffer. The effect of carrier on both tantalum and tungsten distributions was determined using solutions containing Ta-182 and W-181 as tracers. Ten μg of tantalum and t μg of tungsten were injected in these experiments.

The use of varying mixtures of hydrochloric acid and hydrogen peroxide to elute the generator column showed that the yields of tantalum were essentially independent of peroxide concentration, but that breakthrough of the tungsten was inhibited by the presence of peroxide in the eluting solution. Using a constant level of hydrogen peroxide (0.05%), a minimum concentration of 0.05N HCl is required for reasonable yields of the tantalum daughter.

In a typical elution profile for Ta-178 from a 9 ml resin-bed percolated with a solution of 0.15N HCl-0.05% $H_2O_2$, approximately 88% of the eluted activity appears between the second and sixth milliliter of eluant, while one column volume collects 87% of all Ta-178 originally in equilibrium with the W-178. Although the peak profile is sharp, some tailing of the tantalum activity is evident.

The behavior of the W-178 adsorbed on a 9 ml column eluted with the 0.15N-0.05% $H_2O_2$ was determined. Up to a volume of approximately 420 ml, the level of tungsten breakthrough, expressed as a percentage of the tungsten loaded on the column, lies below the detection limit imposed by the experimental conditions (0.0015%), and after 500 ml, it becomes appreciable (ca. 0.05%). Table II shows the variation of W-178 breakthrough observed in one column volume as a function of hydrochloric acid normality and the proportion of hydrogen peroxide. The results using 1N HCl clearly show the need for peroxide in the eluting solution, with 0.005% reducing breakthrough from 1.7%/ml to 0.03%/ml. It appears that a minimum of 0.05% is required to bring breakthrough to acceptably low levels. A comparison of the breakthrough figures obtained with distilled water and 1N HCl shows that W-178 is released significantly more easily as the hydrochloric acid normality is increased.

This finding is underlined by the W-178 batch equilibration experiments. At a constant level of 0.05% $H_2O_2$, the distribution coefficient $K_D$ decreases markedly with increasing normality of the HCl. Similar Ta-182 tracer studies again showed the lack of dependence on the normality of the HCl. The necessity for the presence of $H_2O_2$ was demonstrated in one column loaded with W-178 and eluted with 0.15N HCl. Early breakthrough of tungsten was detected. Changing the eluant to 0.15N HCl-0.05% $H_2O_2$ led to no further detectable losses of tungsten until very large volumes of eluant had been percolated through the column.

With the columns having a 0.6 ml resin bed, an eluant consisting of 0.1N HCl and 0.1% $H_2O_2$ was used because of the higher $K_D$ value of tungsten in the more dilute HCl solution, and because of the more effective stabilization of tungsten by the higher level of hydrogen peroxide. The overall tantalum yield under these conditions was 74% per column volume. The elution profile for this size of column typically showed the integrated yield to be 75% of the total in the first 0.4 ml and 80% in the first 0.6 ml of eluant. Continuous elution of this column showed a level of 0.01% W-178 breakthrough per milliliter after approximately 80 column volumes. The compromise between tungsten breakthrough and tantalum yield is illustrated by the fact that elution of this column with 0.05N HCl-0.05% $H_2O_2$ solution allows double this number of column volumes to be passed before this level of breakthrough occurs. The tantalum yield, however, was reduced to 66% under these conditions.

TABLE II

VARIATION OF W-178 BREAKTHROUCH WITH HYDROCHLORIC ACID CONCENTRATION AND PERCENTAGE OF HYDROGEN PEROXIDE

| $N_{HCl}$ | % $H_2O_2$ | % W-178 Breakthrough |
|---|---|---|
| 0 | 0 | <0.001* |
|   | 0.05 | <0.001 |
| 0.01 | 0.05 | <0.001 |
| 0.025 | 0.05 | <0.001 |
| 0.050 | 0.05 | <0.001 |
| 0.15 | 0.05 | <0.001 |
| 1.00 | 0 | 1.7 |
|   | 0.005 | 0.03 |
|   | 0.05 | 0.008 |
|   | 0.20 | <0.005 |

* % breakthrough = $\frac{\text{W-178 breakthrough/ml eluant}}{\text{W-178 added to the column}} \times 100$.

TABLE III

DISTRIBUTION IN RATS OF CARRIER-FREE Ta-178 SOLUTIONS 15–20 MIN AFTER I.V. ADMINISTRATION

|  | Ta-178 eluate in 0.1N HCl-0.1% $H_2O_2$ | Carrier-free Ta-178 in phosphate Buffer pH 7.0 | Carrier-free Ta-178 in citrate buffer pH 5.4 |
|---|---|---|---|
| Blood | 51.0* | 37.0 | 20.0 |
| Liver | 4.0 | 13.0 | 2.5 |
| Lungs | 1.2 | 1.0 | 1.0 |
| Spleen | 0.4 | 0.5 | 0.1 |
| Heart | 0.7 | 0.4 | 0.3 |
| Kidneys | 0.8 | 1.7 | 1.2 |
| Muscle | 13.0 | 11.0 | 16.5 |
| Bone | 10.0 | 4.0 | 11.0 |
| Skin & Fat | 7.0 | 8.0 | 20.5 |
| Urine | 6.0 | 7.0 | 15.0 |
| Recovery | 94.1 | 83.6 | 88.1 |

*Percentage of injected dose per organ, an average of five animals

A typical gamma-ray spectrum of the eluted Ta-178, obtained with a Ge(Li) detector shows the absence of characteristic tantalum radiation produced as a result of the electron-capture decay of the parent W-178.

Table III shows the organ distribution of Ta-178 (eluted with 0.1N HCl-0.1% $H_2O_2$) at 15–20 min after i.v. administration. In the first column, the results are those for the unmodified eluant, in the second for eluant adjusted to pH 7 with phosphate buffer, and in the third, for solution treated with citrate buffer (pH 5.4). The most significant differences between the three carrier-free tantalum preparations lie in blood, liver, skin, fat, fur, and urine levels.

The effects of added carrier on the distribution of tantalum and tungsten solutions are shown in Table IV. The first two columns give the results obtained with Ta-182 solutions at pH 7 (phosphate-buffer) and pH 5.4 (citrate buffer). Liver activity levels are somewhat lower in the case of the citrate solution, but skin, fat, and fur are higher. Comparisons with the corresponding carrier-free results in Table III indicate no essential differences in either case. The carrier phosphate Ta-182 solution has somewhat elevated bone and liver levels compared with the carrier-free preparation, but this could be due to increased sequestration of colloidal material at the late time of sacrifice (30 min).

The third and fourth columns in Table IV show the results obtained with carrier solutions of W-181 and carrier-free solutions of W-178, both buffered to pH 5.4 with citrate. Again, no significant differences can be seen in the two distributions, the most salient feature of both being rapid clearance through the kidneys.

Ta-178, the short-lived daughter of W-178 can be used for radionuclide imaging using the high-atmosphere multiwire proportional counter. The ion-exchange separation, which is the basis of the generator system, gives good yields of Ta-178 and acceptably low yields of parent breakthrough.

TABLE IV

DISTRIBUTION IN RATS OF CARRIER W-181 AND Ta-182 AND CARRIER-FREE W-178 SOLUTIONS 30 MIN AFTER I.V. ADMINISTRATION

|  | Ta-182 & carrier in phosphate buffer pH 7.0 | Ta-182 & carrier in citrate buffer pH 5.4 | W-181 & carrier in citrate buffer pH 5.4 | W-178 in citrate buffer pH 5.4 |
| --- | --- | --- | --- | --- |
| Blood | 23.0* | 25.3 | 4.9 | 2.7 |
| Liver | 19.4 | 8.5 | 5.6 | 4.4 |
| Lungs | 6.4 | 1.1 | 0.3 | 0.3 |
| Spleen | 0.8 | 0.1 | 0.1 | 0.1 |
| Kidneys | 3.1 | 1.2 | 2.8 | 2.5 |
| Muscle | 13.8 | 16.9 | 7.0 | 7.2 |
| Bone | 13.1 | 9.0 | 14.6 | 20.0 |
| Skin & fat | 9.5 | 21.6 | 12.2 | 7.0 |
| Urine | 4.1 | 8.0 | 44.0 | 50.0 |
| Recovery | 93.2 | 81.7 | 91.5 | 94.2 |

*Percentage of injected dose per organ, an average of two to three animals.

What is claimed is:

1. A physiologically acceptable aqueous solution of tantalum-178 comprising from about 0.1 to 200 millicuries per milliliter of tantalum-178 solution.

2. The process for obtaining a physiologically acceptable aqueous solution of tantalum-178 which comprises binding tungsten-178 to an anion-exchange resin from a hydrochloric acid-solution containing hydrogen peroxide whereby tantalum-178 is formed in situ from said tungsten-178, eluting said tantalum-178 from said resin with an aqueous HCl solution containing hydrogen peroxide and neutralizing the aqueous HCl solution containing tantalum-178.

3. The process of claim 2 wherein said tungsten-178 is obtained by exposing tantalum-181 to incident proton energy of between about 32 MeV and 40 MeV.

4. The process of claim 3 wherein said proton energy is 34 MeV.

5. A kit for the preparation of a physiologically acceptable solution of tantalum-178 from a resin column containing bound tungsten-178 which comprises a first container having a volume of about 1 to 3 ml in which is aseptically and hermatically sealed a 0.05 to 0.25N HCl solution containing from about 0.05 and 3 volume percent of hydrogen peroxide and a second container having a volume of about 0.5 to 3 ml and in which is sealed a neutralizing agent for said acidic solution.

6. The kit of claim 5 wherein the second container is partially evacuated.

7. The kit of claim 6 wherein the second container is provided with a hypodermic syringe.

8. The kit of claim 6 wherein said neutralizing agent is sodium bisulfite.

* * * * *